United States Patent [19]
VonBargen

[11] Patent Number: 5,351,322
[45] Date of Patent: Sep. 27, 1994

[54] FIBER OPTIC PROBE

[75] Inventor: Kenneth P. VonBargen, Berwyn Heights, Md.

[73] Assignee: NIRSystems Incorporated, Silver Spring, Md.

[21] Appl. No.: 136,283

[22] Filed: Oct. 15, 1993

Related U.S. Application Data

[62] Division of Ser. No. 931,783, Aug. 18, 1992, Pat. No. 5,278,412.

[51] Int. Cl.$^5$ .......................... G02B 6/26; G02B 6/32
[52] U.S. Cl. ..................................... 385/12; 385/31; 385/33; 385/34; 385/76; 385/115; 385/116; 385/119; 385/139
[58] Field of Search ....................... 385/12, 14, 15, 27, 385/31, 33, 34, 36, 76, 77, 84, 115, 116, 117, 119, 139; 250/227.11, 227.14, 227.2, 227.24, 343, 341; 426/231, 232, 233

[56] References Cited

U.S. PATENT DOCUMENTS

| | | | |
|---|---|---|---|
| 3,814,081 | 6/1974 | Mori | 385/12 X |
| 4,039,845 | 8/1977 | Oberhänsli et al. | 385/12 X |
| 4,422,321 | 12/1983 | Müller et al. | 385/12 X |
| 4,560,286 | 12/1985 | Wickersheim | 374/131 |
| 4,788,967 | 12/1988 | Ueda | 385/119 X |
| 4,812,003 | 3/1989 | Dambach et al. | 385/12 X |
| 5,087,109 | 2/1992 | Ishizuka et al. | 385/34 |
| 5,096,671 | 3/1992 | Kane et al. | 385/12 X |
| 5,221,839 | 6/1993 | Braun | 250/227.24 |
| 5,278,412 | 1/1994 | DeThomas et al. | 250/343 |
| 5,279,793 | 1/1994 | Glass | 385/12 X |

FOREIGN PATENT DOCUMENTS

| | | | |
|---|---|---|---|
| 0085143 | 8/1983 | European Pat. Off. | 385/12 X |
| WO90/08818 | 8/1990 | PCT Int'l Appl. | 385/12 X |
| WO91/03715 | 3/1991 | PCT Int'l Appl. | 385/12 X |
| WO92/09881 | 6/1992 | PCT Int'l Appl. | 385/12 X |
| 2232484 | 12/1990 | United Kingdom | 385/12 X |

OTHER PUBLICATIONS

Patent Abstracts of Japan, vol. 10, No. 335 (C-384), Nov. 13, 1986.

*Primary Examiner*—Brian Healy
*Attorney, Agent, or Firm*—Lane, Aitken & McCann

[57] ABSTRACT

In a system for measuring moisture content of powder, such as powdered milk while the powder is being dried, the powder is contained in a fluidized bed and a fiber optic probe is inserted through the wall of the container of said bed to be immersed in the fluidized bed. The fluidized bed continuously scrubs the outer surface of the probe window and prevents it from being coated with the powder. Near infrared light is transmitted through a cable optic fiber and said probe to irradiate the powder in said fluidized bed and is reflected back from the powder into said probe and transmitted by said fiber optic cable to a spectroscopic analyzing instrument. The fiber optic probe includes a sapphire rod having a back surface abutting the end of the fiber optic cable and an angled front surface. The front of the probe is closed by a quartz window spaced from the angled front surface of the sapphire rod and held in position by an inwardly directed flange on the outer tubular casing of the fiber optic probe. The front window is provided with an outwardly directed flange and an O-ring is sandwiched between the flange on the window and the inwardly directed flange on the distal end of the probe to provide a seal to prevent powder from getting in the probe.

6 Claims, 2 Drawing Sheets

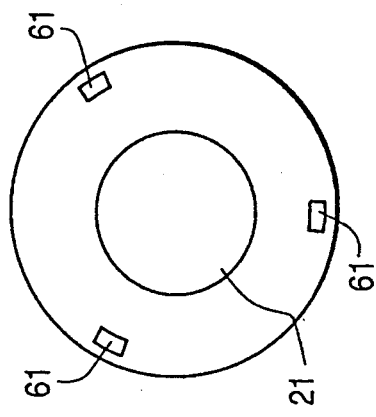
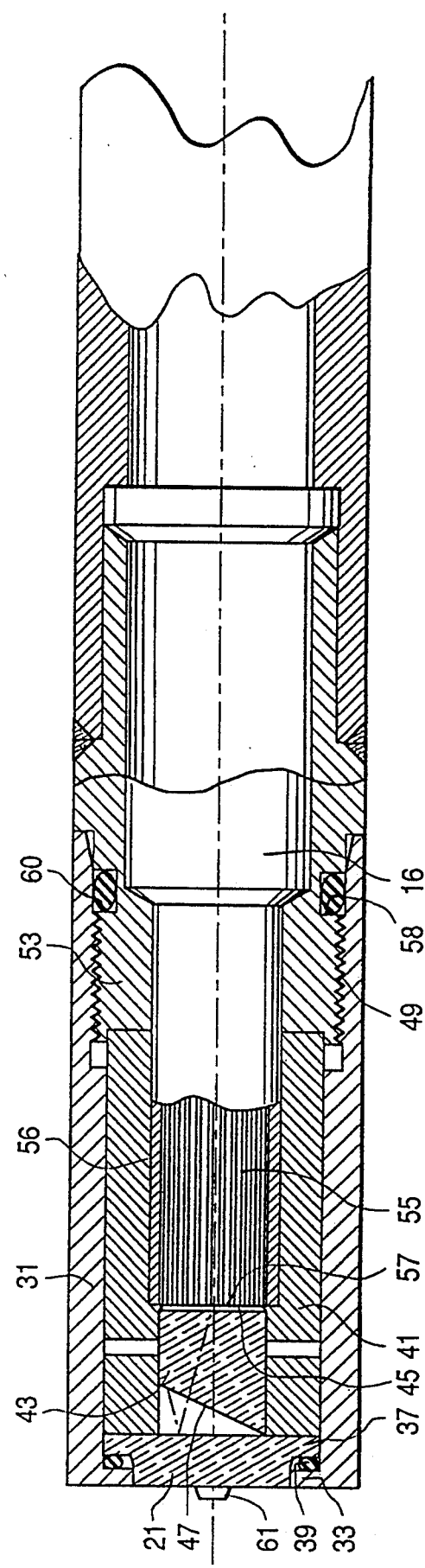

FIBER OPTIC PROBE

This is a division of application Ser. No. 07/931,783 filed Aug. 18, 1992, now U.S. Pat. No. 5,278,402.

This invention relates to an improved system for measuring the moisture content of powder and to a fiber optic probe used in the measuring system.

BACKGROUND OF THE INVENTION

One method of measuring moisture content in powder is by means of near infrared spectral analysis in which the powder is irradiated with near infrared light, the light diffusely reflected from the powder is spectrally divided into its narrow band components, and then mathematically analyzed to provide an accurate measurement of moisture content. However, initial attempts to use near infrared spectral analysis to measure the moisture content of some powder, such as powdered milk, have been unsuccessful because the window through which the near infrared measurements were taken, quickly became coated with the powder and prevented transmission of infrared light between the powder and the instrument where the infrared light is to be analyzed.

SUMMARY OF THE INVENTION

The present invention overcomes the problem of measuring the moisture content of powder by means of a specially designed fiber optic probe which extends into a fluidized bed of the powder beneath the surface of the powder. The powder is contained in a fluidizing chamber in which air is caused to flow up through the powder fluidizing it. The window of the fiber optic probe does not become coated with the powder because the agitation of the granules of the powder continuously scrub the window and prevent the window from being coated with the powder. As a result, the infrared light can be transmitted through the probe, be diffusely reflected from the powder and be transmitted back to a spectral analysis instrument and be analyzed for moisture content.

The fiber optic probe comprises a fiber optic cable which connects the probe to an instrument housing in which a near infrared light source is positioned to transmit near infrared light through transmitting optical fibers of the cable to the probe. The infrared light is transmitted through a window in the distal end of the probe to the powder in the fluidized bed impinging upon the window. The infrared light diffusely reflected from the powder is transmitted back through the window into receiving optical fibers in the cable and carried by the receiving optical fibers back to the instrument housing where the infrared light is analyzed spectroscopically to obtain a measurement of the moisture content of the powder.

In the fiber optic probe, the optical fibers of the cable are terminated in a plane and abut a planar proximal end face of a sapphire rod which transmits near infrared light. An index of refraction matching oil is provided in the interface between the ends of the optic fibers and the sapphire rod. The distal end of the sapphire rod is angled at an angle to refract the light passing through the distal end face of the sapphire rod at an angle of one-half the maximum acceptance angle of the optic fibers. The distal end of the probe is terminated in a quartz window which has parallel inner and outer walls and which is arranged perpendicular to the axes of the ends of the optical fibers in the probe. As a result of the angled end of the sapphire rod, any light specularly reflected from the end of the sapphire rod is prevented from being received by the receiving ends of the optic fibers in the fiber optic cable terminating in the probe. Also, the use of a quartz window in the distal end of the probe prevents light from being specularly reflected from the walls of the window. Accordingly, no specular reflected light will be transmitted back to the instrument.

The quartz window is provided with a flange which cooperates with an inwardly extending flange from the outer casing of the probe at the distal end thereof to provide a positive support at the distal end of the probe for holding the quartz window in the probe. The quartz rod is mounted in a cylindrical sleeve which fits within the outer casing of the probe and holds the flange of the quartz window against the inwardly directed flange at the distal end of the probe casing. An O-ring is provided sandwiched between the flange of the quartz window and the inwardly directed flange of the probe casing to seal the probe against any powder and other foreign matter from getting within the probe. This construction thus positively mechanically locks the window in position and eliminates any possibility of the window coming loose as it might in the case of a window being glued in place at the distal end of the probe. There is no glue at the window to be subject to deterioration by action of the heat of the fluidized bed.

The fiber optic probe is an improvement over an earlier version of the probe wherein the exterior surface of the sapphire rod itself is used as the exterior window of the probe. In this prior version of the probe, the angle of the distal surface of the sapphire rod is approximately at the maximum acceptance angle of the optic fibers and, as a result, any specular reflected light from the window of the sapphire rod or from granules of powder aligned with the window are reflected back to the optic fibers at the maximum acceptance angle of the fibers and therefore are not transmitted back to the spectroscopic analyzing system.

BRIEF DESCRIPTION OF THE DRAWINGS

FIG. 2 is an axial sectional view of the fiber optic probe used in the system of FIG. 1; and FIG. 3 is an end view in elevation of the fiber optic probe.

DESCRIPTION OF A PREFERRED EMBODIMENT

Figure 1:
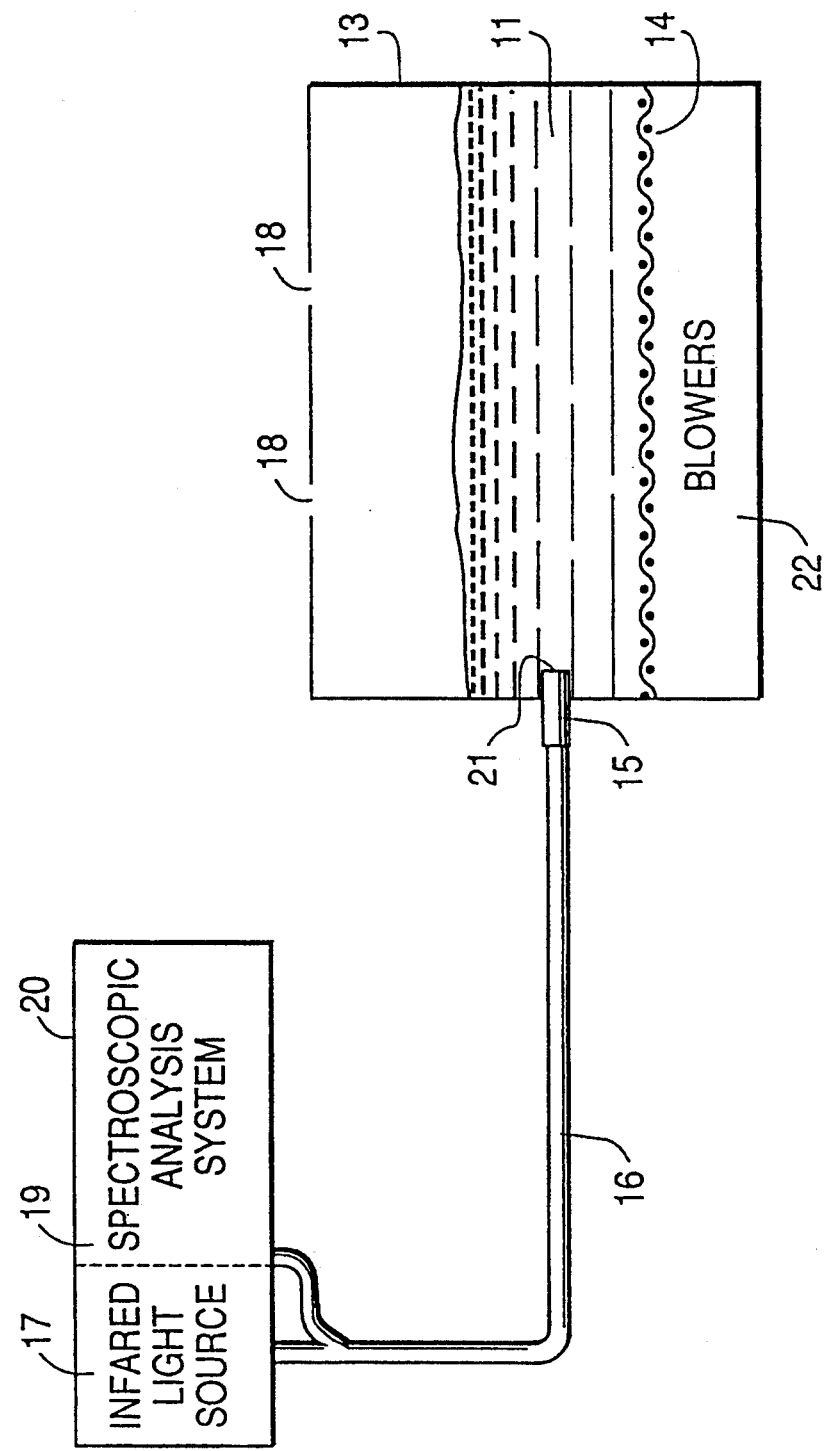
FIG. 1 schematically illustrates the bed of powder measuring system of the present invention.

As shown in FIG. 1, a fluidized bed of powder 11, for example, powdered milk, is contained within a fluidized bed chamber 13. The powder is maintained fluidized within the chamber 13 by means of air introduced into the chamber 13 through a mesh bottom wall 14 of the chamber by blowers 22 located beneath the mesh bottom wall 14. The air passing through the powder fluidizes the powder and, after passing through the bed of fluidized powder, is vented from the chamber 13 through vents 18 in the top of the chamber. The air in addition to fluidizing the powder also serves to dry the powder. A fiber optic probe 15 extends through the wall of the chamber and is connected by means of a fiber optic cable 16 to an infrared light source 17 in a spectroscopic analysis instrument housing 19. A spectroscopic analysis system 20 is contained within the housing 19. This system could be an infrared measuring analysis system, such as marketed by NIRSystems as NIRSystems model No. OL 5000 or Model No. OL 6500. Light from the infrared source 17 is introduced into transmitting optical fibers in the fiber optic cable 16. The transmitting optical fibers carry the infrared light to the probe 15, where the infrared light irradiates the powder in the fluidized bed 11 impinging on a window in the fluidized bed 11 at the distal end of the probe 15. Light diffusely reflected from the powder 21 is received by the probe 15 and by receiving optical fibers in the cable 16 and terminating in the probe 15. The received infrared light is carried by the receiving optical fibers back to the housing 19 where the received diffusely reflected light is analyzed by a spectroscopic analyzing system 20.

The fluidized bed of the powder 11 will be in an agitated state caused by the drying air blowing through the mesh 14 and through the bed of powder 11. As a result of this agitation, the powder will continuously scrub the window 21 and prevent the window 21 from being coated with the powder. Thus, measurements of the powder can be made continuously as the powder is dried. In the preferred embodiment, the powder is dried and measured in a continuous process with new moist powder introduced into one part of the bed and dry powder exiting the bed from the other end. Alternatively, the measurement may be made in a system in which the powder is dried in a batch process.

The spectral analyzing system 19 divides the received infrared light into narrow band spectral components and measures the amplitude of these components. These measurements represent the reflectance of the sample at incrementally spaced wavelengths. From these measurements and corresponding measurements made from a standard sample, the NIRSystems Model No. OL 5000 instrument or the NIRSystems Model No. OL 6500 instrument can determine the percentage of moisture in the powder by well known mathematical processes. For example, the instrument can determine the absorbance of the powder at each of the incremental wavelengths by comparing the reflectance measured from the powder with the reflectance from the sample at each wavelength. The instrument can then determine the percentage of moisture in the powder from the absorbance determined at one or more selected wavelengths from a mathematical formula, such as:

% of moisture = $Ax + B$, in which A and B are constants and x is the absorbance of the powder at the selected wavelength.

As shown in FIG. 2, the fiber optic probe comprises a tubular outer housing 31 at the distal end of the probe provided with in inwardly directed flange 33. A quartz window 21 is positioned in an opening defined by the inner annular edge of the flange 33. The quartz window has planar inner and outer surfaces perpendicular to the axis of the probe and the outer surface of the window projects slightly beyond the outer surface of the flange 33. This feature, or alternatively, having the outer surface of the window 21 flush with the outer surface of the flange 33, is important to prevent any powder of the fluidized bed from accumulating on the window. The quartz window 21 is provided with an outwardly directed flange 37 adjacent to its inner surface to coact with the flange 33 to support the window 21 from outward movement at the distal end of the probe. An O-ring 39 is compressed between the flange 37 and the flange 33 and provides a seal to prevent powder from getting inside the probe. A tubular support 41 telescoping with the tubular outer housing 31 is forced against the flange 37 to compress the O-ring 39 between the flange 37 and the flange 33. The tubular support 41 has mounted therein a sapphire rod 43 which has planar front and back faces 45 and 47. The back face 45 is perpendicular to the axis of the probe and the front face 47 is at an angle of 25 degrees to the face 45. The outer casing 31 is provided with internal threads 49 which mate with external threads on a tubular rear housing 53. The tubular rear housing 53 contains the fiber optic cable 16. The rear end of the tubular support 41 terminates at the front end of the threads 49. The housing 53 is provided with a planar annular front end which abuts against a planar rear surface of the tubular support 41. The abutting surfaces of the housing 53 and the tubular support 41 are perpendicular to the axis of the probe. When the housing 53 is fully screwed into the threads 49, the housing 53 will push the tubular support 41 against the flange 37 and compress the O-ring 39. An annular groove 58 is defined in the outer surface of the rear housing 53 and receives an O-ring 60, which is compressed between the housing 31 and the bottom of the groove 58. The O-ring 60 provides a seal to protect against powder getting inside the probe through the interface between the housing 31 and the rear housing 53.

The fiber optic cable 16 passing through the housing 53 comprises optical fibers 55 contained within a tube 56. The optical fibers 55 terminate at their distal end in a planar end face 57 with their axes at the end face parallel to the axis of the probe. The end face of the optical fibers abuts the rear planar surface 45 of the sapphire rod 43 when the housing 53 is fully screwed into the threads 49. Index of refraction matching oil is provided in the interface between the planar end face 57 of the optical fibers 55 and the rear end face 45 of the sapphire rod 43.

The angled front face 47 of the sapphire rod 43 serves to prevent light specularly reflected from the front surface 47 of the sapphire rod from being received by the optical fibers 57 because the specularly reflected light is at the maximum acceptance angle of the optical fibers. Accordingly, the specularly reflected light is not received and transmitted by the optical fibers.

The rod 43 may be made of other infrared transmitting materials instead of sapphire. However, the window 21 must be of a relatively low index of refraction material and sapphire is not a satisfactory material for the window 21 because of the relatively high index of refraction of sapphire. If a sapphire material were used for the window 31, too much light would be specularly reflected from the surfaces of the window and the probe would not efficiently transmit light to the powder being measured.

As better shown in the plan view of the distal end face of the probe illustrated in FIG. 3, the end wall of the outer tubular housing 31 is provided with three feet 61 distributed around the window 21. The feet 61 are for use when the probe is used in connection with measuring constituents in a liquid in a beaker. When the probe is used in this application, a reflectance plate is positioned at the bottom of the beaker and then the probe is rested on the reflectance plate to provide a fixed amount of the liquid in the beaker between the window 21 and the reflectance plate.

The above description is of preferred embodiments of the invention and modifications may be made thereto without departing from the spirit and scope of the invention which is defined in the appended claims.

I claim:

1. A fiber optic probe comprising a fiber optic cable having optical fibers terminating in a planar end face perpendicular to the axes of said optical fibers at said end face, a light transmitting rod having a planar proximal end face perpendicular to the axes of said optical fibers and abutting the end face of said optical fibers, said rod having a distal planar end face positioned at an angle to said proximal planar end face, and a window positioned adjacent to said distal end face of said rod to transmit light transmitted through transmitting optical fibers of said cable and through said rod and to transmit diffusely reflected light to said rod to be transmitted thereby to receiving optical fibers in said cable, said window having inner and outer planar surfaces perpendicular to said axes of said optical fibers.

2. A fiber optic probe as recited in claim 1, wherein said optical fibers are transmissive to near infrared light, said rod is transmissive to near infrared light and said window is transmissive to near infrared light, said window being made of quartz.

3. A fiber optic probe as recited in claim 2, wherein said rod is made of sapphire.

4. A fiber optic probe as recited in claim 1, wherein said window is formed with an outwardly directed flange adjacent to the planar inner surface of said window, and wherein said probe further comprises a tubular casing having an inwardly directed flange at said window and supporting said window against outward movement at said outwardly directed flange, and means within said tubular casing to hold said outwardly directed flange against said inwardly directed flange.

5. A fiber optic probe as recited in claim 4, wherein an O-ring is sandwiched between said outwardly directed flange and said inwardly directed flange.

6. A fiber optic probe as recited in claim 4, wherein said means to hold said outwardly directed flange against said inwardly directed flange comprises a tubular member mounting said rod telescoped within said tubular casing.

* * * * *